US00RE34249E

United States Patent [19]

Divis et al.

[11] E Patent Number: Re. 34,249

[45] Reissued Date of Patent: May 11, 1993

[54] INTERDENTAL IMMOBILIZATION DEVICE

[75] Inventors: Boris Divis, Campbell River; Colin McColgan, Komoka, both of Canada

[73] Assignee: Dimac Medical Inc.

[21] Appl. No.: 668,971

[22] Filed: Mar. 12, 1991

Related U.S. Patent Documents

Reissue of:

[64] Patent No.: 4,968,248
Issued: Nov. 6, 1990
Appl. No.: 338,935
Filed: Apr. 12, 1989

[30] Foreign Application Priority Data

Sep. 27, 1988 [CA] Canada ..... 578613

[51] Int. Cl.[5] ..... A61C 3/00

[52] U.S. Cl. ..... 433/18; 602/17

[58] Field of Search ..... 433/18, 19, 215, 225, 433/149, 178; 128/89 A

[56] References Cited

U.S. PATENT DOCUMENTS 2,481,177 9/1949 Tofflemire ..... 128/89 A
2,502,902 4/1950 Tofflemire ..... 128/89 A
4,202,328 5/1980 Sukkarie ..... 128/89 A
4,355,979 10/1982 Weissman ..... 433/225
4,727,867 3/1988 Knoderer ..... 128/136
4,813,869 3/1989 Gatewood ..... 433/18

OTHER PUBLICATIONS

M. Voldrich, Stomatologicka, Prague, Czechoslovakia.

*Primary Examiner*—Cary E. O'Connor
*Attorney, Agent, or Firm*—Bull, Housser & Tupper

[57] ABSTRACT

An interdental immobilization device consists, in the preferred embodiment, of a longitudinal deformable shaft having a smooth cylindrical portion that terminates as a pointed tip at the distal end and a helical threaded portion at the proximate end. A nut defining an aperture therethrough matingly threads along the helical threaded portion and the length of the deformable shaft is such as to permit the distal portion of the cylindrical portion to encircle the tooth and to loop above the shaft over a segment of the helical threaded portion. In an alternative embodiment, the longitudinal shaft has a detent at the proximate end and there are anchoring fixtures in the form of truncated conics which are adapted to travel along the shaft. One of the fixtures anchors in the detent and the other, is engaged against adjacent teeth by the nut, when the nut is turned down on the helical thread. The conics provide a bearing surface adapted to carry interconnecting elements such as wires or elastics for staplizing the jaw.

51 Claims, 4 Drawing Sheets

INTERDENTAL IMMOBILIZATION DEVICE

Matter enclosed in heavy brackets [ ] appears in the original patent but forms no part of this reissue specification; matter printed in italics indicates the additions made by reissue.

This invention relates to an interdental immobilization device.

From time to time, it is necessary to immobilize the human jaw.

This will be necessary when fractures of mandible occur or when (sparingly) one wishes to have their mouth fixed shut so as to avoid eating, and hence lose weight.

The existing method of the prior art uses a pliable metal strip with projecting hooks known as an arch bar and several fine wires and rubber bands. The metal strip is secured tightly to the teeth of the upper jaw by passing a wire around the base of a tooth and through the gum and over each side of the tooth and also over the metal strip. At this point, both ends of the wire are outside the mouth and are twisted together to hold the metal strip urgingly against the outside surface of the teeth. The twisted wire is then cut to a length of approximately ⅛ to ¼ inch and bent backward towards the gum and preferably placed in between two adjacent teeth to prevent irritation on the inside of the lips.

This is repeated spatially around eight to twelve teeth of the upper jaw and the same is repeated over the lower jaw.

The metal strip has the projecting hooks spatially disposed on its outside surface and over these hooks [small]. *Small* rubber bands or wires are then attached between those hooks of the metal strip attached to the teeth of the lower jaw and those hooks of the upper jaw. This technique has been published at pages 301 through 303 in Surgery of the Upper Respiratory System (Vol 1-2nd Edition) by William W. Montgomery M.D., published by Lea & Febiger, Copyright 1979.

This particular prior art technique, which is extremely common in North America and around the world, has several disadvantages. The most dominant disadvantage is that during twist tightening of the wires, the wires can easily snap and the whole process must be repeated hence adding to the length of the installation procedure. It is not uncommon for this procedure to take between 1 and 2 hours of operating theatre time since a general anesthetic for the patient is always needed.

After approximately two days of use, the wires need to be retightened and retwisted as they have a tendency to loosen off and sometimes break. If they break during tightening, the patient must be re-anesthetized again within the operating theatre and new wires inserted as before. Further, the patient must be anesthetized for wire removal after the jaw has mended.

With the recent scare of AIDS and HEPATITIS B, there is a constant danger of trauma to the surgeons hands from the ends of the wire and hence exposure to the patient's body fluids and blood since the passing of the wire between the teeth, always ruptures the gum and the gum bleeds.

The conceived fixtures according to the invention have several advantages over the prior art; namely (a) anesthetic is generally required only on installation of the fixture;

(b) the fixture may be tightened by the simple expedient of turning down a nut on a flexible screw as there is no wire twisting with [these appendant] *the attendant* possibilities of wire breakage and blood letting; thus, the prior art step for re-installation of broken wires in an operating theatre environment with the patient anesthetized is avoided; not to mention the associated blood letting; and, (c) the fixture is easily removed generally without the patient being re-anesthetized.

In one embodiment, the invention is disclosed as a novel three part fixture, and in another embodiment it is a four part fixture; both of these embodiments employ frusto-conical surfaces or alternative truncated cones as a pair, or in combination with a nut and screw. These fixtures expose an anchoring surface associated with the nut, which preferably is cylindrical, onto which rubber bands or wires may be attached so as to fix the lower [and upper] jaw into rigid position.

In a third embodiment, the interdental immobilization device is but a two part fixture, a [yieldable] *deformable* stainless steel shaft with [one] *a proximate* end [as a threaded] *comprising an adjacent* helical [shaft] *threaded portion* that extends into a smooth [continuous shaft] *cylindrical rod* that then tapers into a pointed [tip] *distal end.* [The smooth cylindrical portion of the shaft is capable of being bent and a threaded] *A* nut *defining a channel therethrough* is adapted to threadingly mate [onto the threaded shaft] *with the helical threaded portion* and to tighten down and to locate the shaft and nut in a clamping arrangement about a tooth in a manner as will be described.

In one variant of [both embodiments of] the nut, the nut defines a smooth bored channel sized slightly smaller in diameter than that of the threaded [shaft] *portion*. In this variant, the nut is composed of a plastic material such as nylon. As a further variant of the nut the channel has a shorter major [bore] *portion* with diameter larger than that of the threaded [shaft] *portion* that steps into a longer minor [bore] *portion* with diameter slightly smaller than that of the threaded [shaft] *portion*. The length of the minor [bore] *portion* is substantially greater than that of the major bore. As a further alternative variant of the nut, the nut may have a helically threaded channel of constant diameter which threadingly mates with the helical [thread] *threaded portion* of the [threaded channel of constant diameter which threadingly mates with the helical thread of the screw] *shaft* and is composed of a biologically inert metal such as surgical stainless steel. In these embodiments, it is preferred that the nut have a truncated cone portion with the channel intersecting the truncation, and wherein the truncated cone portion extends into a cylindrical piece bounded by a bearing surface such as a hexagon or knurl. In an embodiment of the [threaded] shaft, the [shaft has means to index itself into] *proximate end is deformed to mate with a slot in* one of the cones [as well as]. *The proximate end is further deformed* to protrude beyond the cone as a bent tip so when fixed between the teeth the bent tip [so when fixed between the teeth the bent tip stands] *extends* as a protrusion in the crevice defined by [these] adjacent teeth.

[The] *In one embodiment of the* invention [therefore contemplates] a two part fixture for interdental immobilization *is provided* comprising:

a longitudinal deformable shaft *comprising a proximate end* defining a helical threaded portion [that extends from one end and that transforms], *said shaft extending* into a smooth cylindrical rod *portion* that terminates at a pointed distal end and a [screw member] *nut* defining a [bore] *channel* therethrough adapted to [matingly thread] *threadingly mate* with the helical threaded portion, the length of the [deformable] longitudinal *deformable* shaft being such [a] *as* to permit the distal portion of the cylindrical rod to encircle a tooth and to loop about the shaft over a segment of the helical threaded portion.

The longitudinal shaft [is] *may be* surgical stainless steel in the preferred diameter of 0.025" to 0.032" [inches and], the [screw member] *nut* is nylon and the [aperture is a step bore which] *channel* steps from a major [bore] *portion* to a minor [bore] *portion*, the minor [bore] *portion* having a diameter [at least equal to the exterior] *smaller than the* diameter of the [stainless steel shaft] *threaded portion.* [In the preferred embodiment, the] *The* [nylon] nut [has] *may have* a frusto-conical surface that extends into a cylindrical bearing portion and defines means for turning such frusto-conical surface.

[The] *In a further embodiment of the* invention a [also contemplates] multi-part fixture for interdental immobilization *is provided* comprising:

(*a*) an elongated [member] *shaft* carrying near one end, a detent and hear the other opposite end, a threaded portion;

(*b*) a first anchor means adapted to engage the detent; *and*

(*c*) a second anchor means defining a body portion and a [bore] *channel*, and adapted to travel on the member, the body portion having a cross-sectional area traverse to the [bore] *channel* that in part, is smaller than at other axial locations along the body portion so as to accommodate and carry interconnecting elements such as wires or elastics.

More specifically, [there is] *the elongated shaft may comprise* an "L" shaped [helical shaft with a distal arm and a] *detent at a proximate end, with* a threaded [shaft] *portion* and a pointed tip thereon [a proximate arm wherein the proximate arm extends] *at the other opposite end. The proximate end of the elongated shaft may extend* through an obtuse angle into [a straight] *an* inclined [piece that acts as a] protrusion. [This shaft] *The proximate end* protrudes through [an] *the first* anchor [member] *means* which in one embodiment is a truncated cone *or conic*. The [screw] *elongated shaft* and [cone are] *conic may be* stainless steel [in the preferred embodiment while the]. *The* second anchor means [in the preferred embodiment includes] *may include* a [capture] *bearing* region and [is] *may be* composed of nylon with a [smaller] *shorter* major [bore] *portion* stepping into a [smaller] *longer* minor [bore] *portion* sized [a] *in* diameter smaller than that of the [screw] *threaded portion* so that the [screw can] *threaded portion may* tap into the minor [bore a helical thread for] *portion to* matingly [securing] *secure* the nut onto the [screw] *threaded portion*. The [screw also carries a capture] *bearing* region [which in its preferred embodiment is] *may be* a circumferential shoulder which acts as a bearing surface *for wires or elastic bands* for interjoining a plurality of said fixtures located spatially between teeth of the upper and lower jaw.

The invention will now be described by way of example and reference to the accompanying drawings in which.

Figure 6:
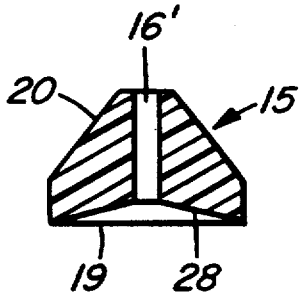

FIG. 6 [illustrates] *is a perspective view illustrating* the securing of the upper and lower jaw according to the prior art.

Figure 4:
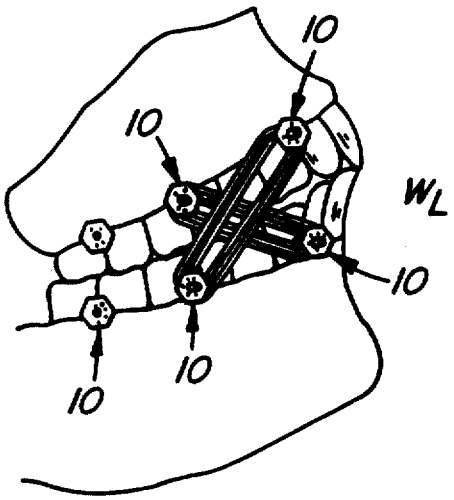
FIG. 4 is a perspective view of the [first step] *lower arch bar* according to the prior art.
Figure 7:
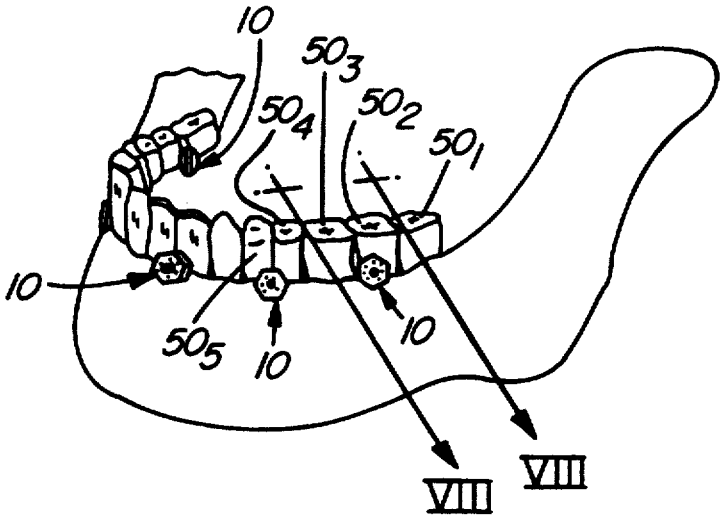

FIG. 7 [corresponds to FIG. 4] *is a perspective view of the three or four part embodiments of this invention* as it relates to [the] implantation [of devices according to the invention] *on the teeth.*

Figure 8:
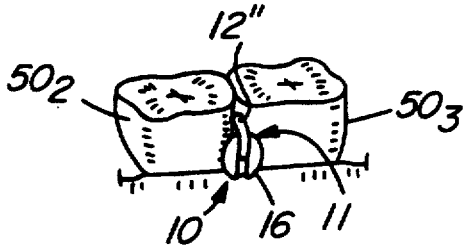

FIG. 8 is a perspective view showing the implantation of [an embodiment] *the three and four part embodiments* of the invention [between teeth] as viewed from the inside of the mouth; and, hence is a view along VIII—VIII of FIG. 7.

Figure 9:
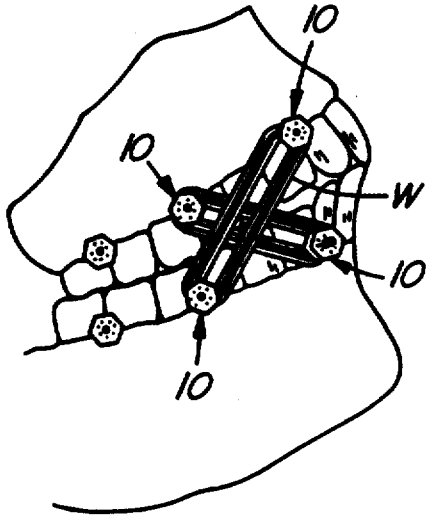

FIG. 9 is a partial perspective view of a jaw indicating the mode of securing the upper and lower jaws according to [the] *this* invention.

Figure 10:
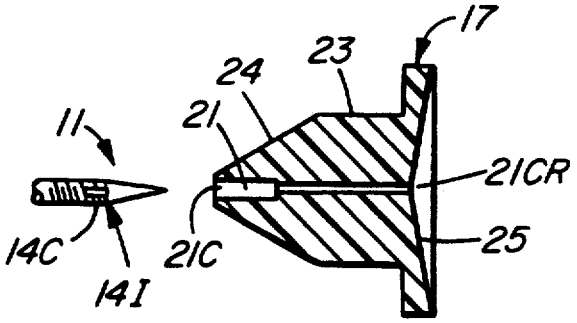

FIG. 10 is a cross-sectional view of one embodiment of the nut *having a shorter major portion and a longer minor portion.*

Figure 11:
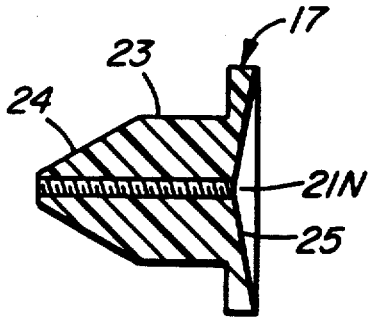

FIG. 11 is a cross-sectional view of another embodiment of *the* nut [according to the invention] *having a helically threaded bore of constant diameter.*

Figure 12:
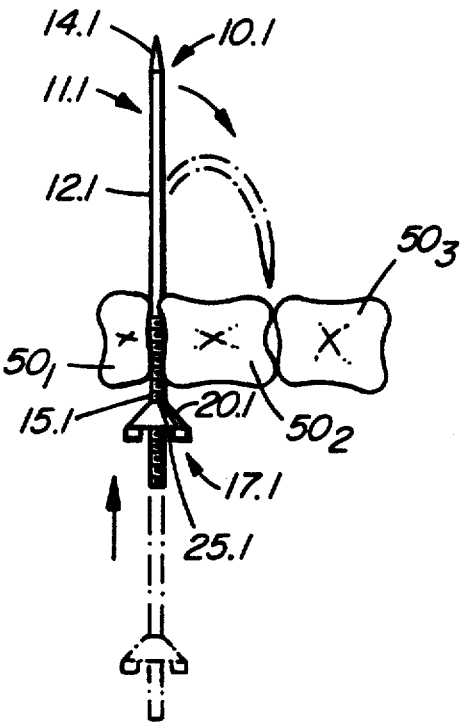

FIG. 12 is a top plan view of the two part device according to the invention shown during its initial stages of installation between two adjacent teeth.

Figure 13:
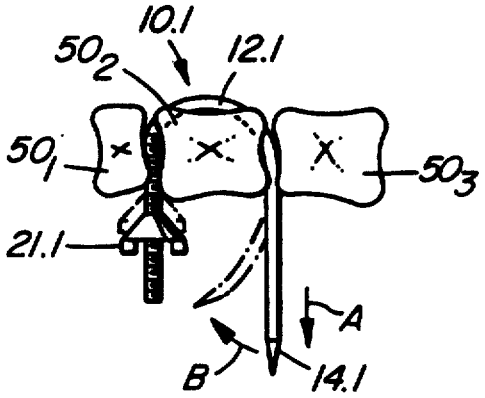

FIG. 13 shows [the second step of the installation procedure of] the two part device *of FIG. 12* where the smooth cylindrical *rod* portion of the shaft has been bent and pushed through the space between said one tooth and the next adjacent tooth.

Figure 14:
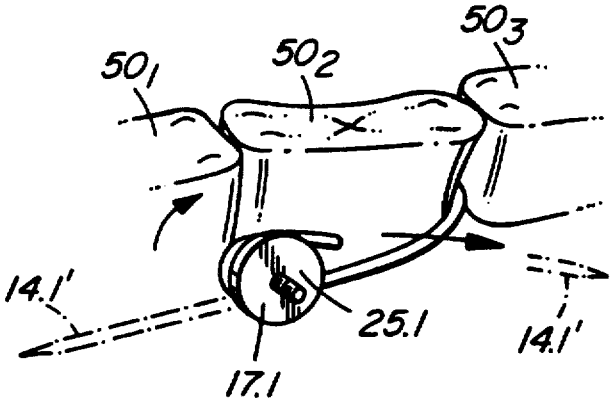

FIG. 14 is a perspective view [indicating the third step of the installation procedure of the two part device] *of the two part device of FIG. 12 where the distal end of the shaft is wrapped about the shaft at the threaded portion.*

Figure 15:
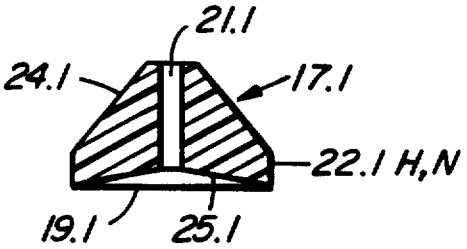

FIG. 15 is a cross section through [an alternative nut] *the nut of the two part device of FIG. 12,* having a smooth uniform bore.

Figure 1:
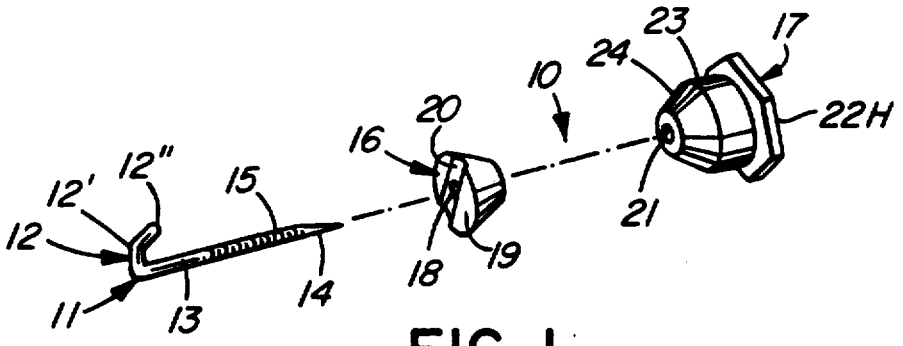
FIG. 1 is a perspective assembly view *of* the three part embodiment of the invention.
Figure 2:
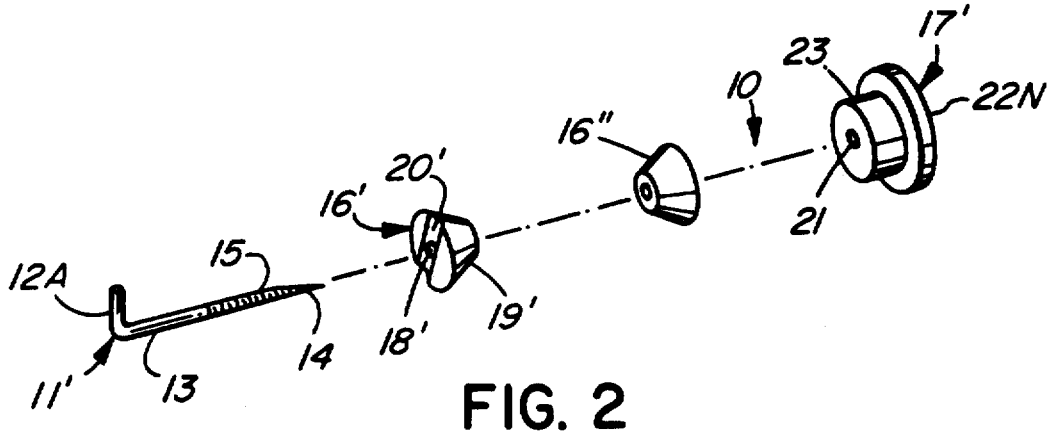
FIG. 2 is a perspective assembly view of the four part embodiment of the invention.

*Referring to FIGS. 1, 2 and 12 alternate embodiments of device 10 are shown. The three part embodiment is shown in FIG. 1 and comprises shaft 11 extendable through cone 16 and attachable to nut 17. The four part embodiment is shown in FIG. 2 and comprises shaft 11' extendable through conics 16' and 16" attachable to nut 17. The two part embodiment is shown in FIG. 12 and comprises shaft 11.1 attachable to nut 17.1.*

*THREE PART DEVICE*

Referring to FIG. 1, the fixture 10, according to the invention, consists of [a U] *an "L"* shaped shaft 11 with an upstanding proximate arm 12 [that] *forming the proximate end of shaft 11. Arm 12* is bent through an obtuse angle *at bend* 12' to [terminate as] *form a detent and which terminates in* a forwardly inclined straight piece 12". [From the proximate arm 12, it] *Shaft 11* extends from the proximate arm 12 as [a] longitudinal shaft *portion* 13 with [its] *the* distal end *of shaft portion 13* tapering to [a] point [at] 14. [Part] *Threaded portion 15* of the shaft [13] *11* is helically threaded [as at 15]. A truncated conic member, or cone 16 consists of a flat bottom 19 through which extends a slot 20 [and the]. *The* cone *16* defines therethrough a channel 18 *or bore* which passes *longitudinally* through the [apex] *center* of the cone [and hence truncates it], as shown in FIGS. 1 and 2. The channel 18 is *of* a diameter slightly larger than the diameter of the shaft *portion* 13 so as to allow free passage therethrough. This is more clearly seen in [the sectional] FIG. 3. The slot 20 [is] *includes outer* outwardly tapered [at 20' at] *ends 20A of* the identical obtuse angle as [at] *bend* 12' so that the proximate arm 12 may appropriately index *or fit* within the slot 20 and the bend 12' and straight [distal] piece 12" mate against the inclined or bevelled surface of [slot 20'] *one of ends 20A* allowing the end of [distal] piece [12'] *12"* to protrude into the crevice defined by the bodies of two adjacent teeth.

Figure 3:
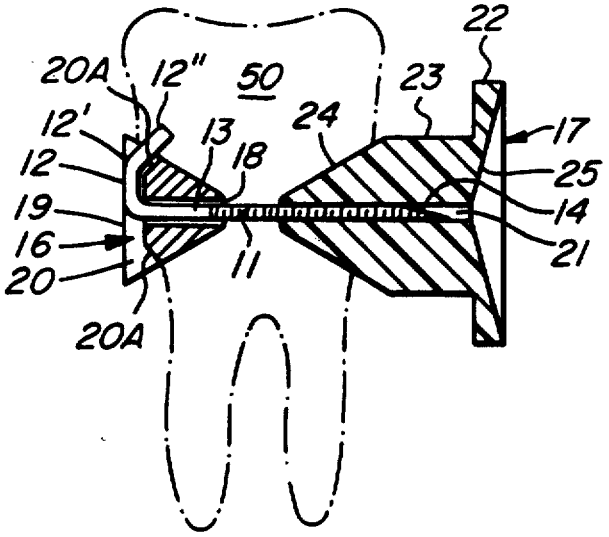
FIG. 3 is a section through the embodiment according to FIG. 1 showing its implantation adjacent a tooth shown in phantom.

The nut 17 [in one of the preferred embodiments, that is] shown in FIGS. 1 and 10, is formed of nylon and [the] *has a* channel 21 *extending longitudinally through the center of nut 17. Channel 21* is a *two* stepped smooth walled channel, as more clearly seen in FIG. 10, with a shorter major [bore] *portion* 21C, [and a longer minor bore 21CR;] the major [bore] *portion* interfacing with the apex [thereof. Also the] *surface of nut 17. The major portion 21C is connected to a longer minor portion 21CR with the diameter of the minor portion 21CR being less than the diameter of shaft 11. Nut 17 is contoured with an inner conic portion 24, an intermediate cylindrical portion 23 and an outer gripping surface 22H. The* nut 17 may be profiled [as seen in FIGS. 1 and 3] *alternately* so as to provide an outer gripping surface [12], *of* either [a] hexagonal gripping surface 22H [sized greater than the diameter of the cylindrical shoulder 23 through which it steps into a truncated conical section 24, or as seen in FIG. 2, a knearl gripping surface], *as seen in FIG. 1 or knurled circular gripping surface 22N. Gripping surface 22H and* 22 N *provide a shoulder to retain wires or loops W (FIG. 9) against shoulder 23, when in use.*

[The] *Outer* face *25* of the nut [obverse to the truncated conic 24] *17 adjacent gripping surface 22H* is conically recessed [at 25] as more clearly seen in FIG. 3 (see also FIGS. 10 and 11). If the tip 14 of the shaft [13] *11* extends into the *recess formed by* conical [recess] *face* 25 after the physician has placed the fixture 10 between teeth, as will be disclosed hereafter, the physician has room to insert a pair of diagonal cutters 30 (see FIG. 3A) or the like, into the recess [25]; and, to snip off the protruding segment of shaft [13] *11* and the tip 14 which are collectively shown as SR so as not to cause abrasion to the inner skin of the mouth.

Referring to FIGS. 3 and 8, in application, the shaft 11 is fitted to slip through *channel 18 in* cone 16 with the proximate arm 12 indexing into the slot 20. The shaft 11 is pushed between the base of two adjacent teeth 50 ($50_2$ and $50_3$ in FIG. 8) and the point 14 assists in the penetration of the shaft 11 from the inside of the mouth *outwardly* through *or above* the gum mass between said teeth $50_2$ and $50_3$ to the outside gum surface. The nut 17 is then, if hexagonally formed as in FIG. 1, put into a socket wrench and threaded onto *portion 15 of* the shaft 11 so as to urge against the adjacent teeth $50_2$ and $50_3$ as well as the adjacent gum mass. If the profiled nut of FIG. 1 [having the hexagonal surface 22H] is nylon, and has the stepped bore channel *21*, shown in FIG. 10, the tapered tip 14 of the [screw] *shaft* 11 indexes into the opening face of the major [channel] *portion* 21C and as the nut is rotated, the shaft 11 itself taps a helical thread into the wall of the minor [bore] *portion* 21CR of the nylon nut of FIGS. 1[, 3] and 10 and secure anchoring is thereby achieved. As the nut 17 is turned tighter, the cone 16 and the conic section 24 of the nut 17 are drawn toward each other and a tight fit is achieved. If there [be] *is* any loosening off *of nut 17* at a later time it is simple to just *by* slightly [turn] *turning* down the nut *17* with the socket wrench.

This step is repeated to locate, as shown in FIG. 7, a plurality of fixtures 10 mounted between teeth along the lower jaw. The steps are repeated in relation to the upper jaw.

The [shoulder] cylindrical [surface] *portion* 23 of the nut 17 is used as the capture *or bearing* region for anchoring wire *or elastic loops* W, which is laced between top and bottom fixtures as shown in FIG. 9. In this way, the lower jaw is immobilized to the upper jaw. This wrapping may just be accommodated by weaving or wrapping of wire [(W)] or [if preferred,] elastic loops [$W_1$] *W*, may be used.

Figure 5:
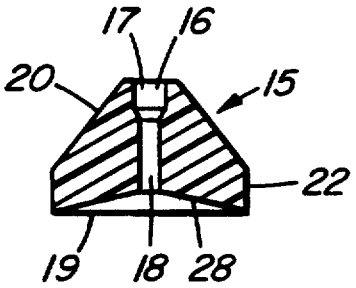
FIG. 5 is a *top* plan view of the [brace] *lower arch bar* according to the prior art *secured by wire to teeth.*

According to the prior art, and referring to FIG. 4 through FIG. 6, the elastic loops [$W_1$] are wrapped over hooks H, spatially disposed along a flexible stainless steel arch bar HB which is placed at the gum line on the facial side of the teeth and secured there by wire [$W_{(i)}$] *W* which wrap around a single tooth and extend between adjacent teeth and are twisted over the front or facial portion of the arch bar, as more clearly seen in [FIG.] *FIGS. 4 and 5.*

*FOUR PART DEVICE*

Referring to FIG. 2, [a further] *an* alternative embodiment [consists of] *incorporates* two identical truncated stainless steel conics [shown as] 16' and 16". The shaft [11] *11'* has [but] a proximate straight arm [12] *12A* and that arm indexes into the slot [20] *20'* of the truncated conic 16'. The nut [17] *17'* is fashioned without [a] *the* tapered conic section 24 [and hence a] *of the three part embodiment of FIG. 1. A* flat bearing as shown *in FIG. 2 is provided* and [for reason,] a second conic 16" identical to [that of] *conic* 16' is used as the bearing member for the nut. Similarly, as disclosed relative to FIG. 1, the shaft [11] *11'*, the conics 16' and 16" and nut [17] *17'* may be installed between the teeth. This particular embodiment is less favourable to that of [FIGS. 1 and 10] *FIG. 1* since there are four rather than three discrete components [to consists of] *including* two identical truncated stainless steel conics [shown as] 16' and 16". The shaft [11 has but] *11' is L shaped with* a proximate straight arm [12 and that] *12A which* arm *12A* indexes into the slot [20] *20'* of the truncated conic [1]. [a further embodiment consists two identical truncated stainless steel conics shown as 16' and 16". The shaft 11 has but a proximate straight arm 12 and that arm indexes into the slot 20 of the truncated conic 1 surface 24.]

Figure 3A:
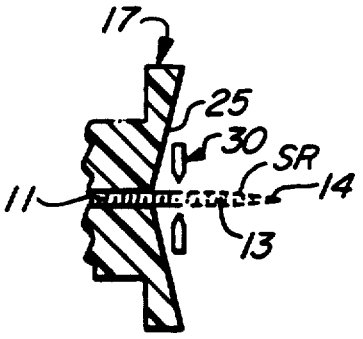
FIG. 3A is a partial section of a longer [screw] *shaft* in the nut of FIG. 3 showing how the [screw] distal end is severed after implantation.

Referring to FIG. 3A *which refers to the three part embodiment of FIG. 1*, the length of the shaft 11 may be structured [quite] *sufficiently* long so as to accommodate various depths [(thicknesses of teeth)] *(thicknesses) of teeth.* In *the* instance *depicted in FIG. 3A*, the tip 14 of the shaft 11 protrudes well beyond [the] face of the [conical recess 25 of the nut as shown in FIGS. 3 and 3A] *nut 17.* [This overhang extent] *The protruding segment* SR may be cut off with a pair of wire cutters 30 as shown in FIG. 3A. This provides means for reducing the length of the [screw] *shaft 11* each time that the nut 17 is turned down on the teeth to tighten the fixture. Abrasion to the inner lip and cheek is thus avoided. *This applies equally to the four part embodiment of FIG. 2.*

Returning now to FIG. 10, when the nut is composed of nylon, the channel may be a two step bore as shown, that is a shorter major [bore] *portion* 21C that steps into a longer minor [bore] *portion* 21CR. The thread *portion* 15 of the shaft 11 may be modified (though not required) near its tip 14 with a cup [at] 14C and a protruding piece 14I which cooperatively acts as a "tap". When the nylon nut [10] *17* is turned down on [this] end [taped threaded shaft of] *14, cup 14C and piece 14I cause* the shaft 11' [the shaft 11' ] *to* self [taps] *tap into* the minor [bore ] *portion* 21CR to form a mating thread therein securing the nut 17 [thereon] *to shaft 11.*

In the preferred embodiment of *the nut 17 shown in* FIG. [FIGS. 1, 3 and] 10, the shaft 11[,] and cone 16, are stainless steel and the nut 17 is made of nylon. We have found that a cone *16* base diameter of approximately 5 m.m. and a cone *16* height of 3 m.m. is satisfactory with an angle of 40°. This means that the hexagon diameter 22H of the nut 17 is preferably about 7 m.m.[;] while the shoulder portion 23 diameter is about 5 m.m. with a depth of shoulder *to the outer diameter of surface 23H or 23N* of about 2 m.m. to allow adequate space for winding of wire or elastics [$W_1$] *W* between respective [shoulders] *shoulder portions 23* of fixtures *10* in a manner as seen in FIG. 9. [In this respect the] *The* preferred length of [the] shaft *11* is about 12 m.m. with [the shaft] arm 12 having a length of approximately 2.5 m.m. and [protrusion] *piece* 12" of about 2.5 m.m. and an outside bend diameter at 12' of 0.8 m.m. In this respect, slot 20 cut into the [face of the base] *bottom 19* of the cone *16* has a preferred depth of approximately 1 m.m. and a preferred width of between 0.8 and 1 m.m.

In a variant of the nut 17, [it] *nut 17* may [be stainless steel as shown in FIGS. 1 and 11. In this instance, the central channel 21 is a uniform helically threaded channel 21N shown in FIG. 10.] *include channel 21 which is a uniform helically threaded channel 21N as shown in FIG. 11.* [The stainless steel nut] *Nut 17* may be profiled with either the hexagonal surface 22H of FIG. 1 or with a cylindrical knurled surface 22N [and] of FIG. 2. *Nut 17 may be of resilient material such as nylon, as indicated in FIG. 11 or of stainless steel or other suitable non-resilient material.*

It should be noted, that if [the formed] shaft 11 of FIG. 1 is used, the [proximate arm] tip of the straight piece 12" protrudes beyond the [conic] *cone* 16 (as shown in FIG. 3) into the crevice defined by the bodies of two adjacent teeth (see FIG. 8) and anchors the [screw] *shaft 11'* preventing its rotation and the corresponding rotation of the [conic] *cone* 16 in FIGS. 1, 3, and 8, as the nut 17 is initially turned down.

If the shaft [11 is of the unmodified shape] *11'* as shown in FIG. 2, *is used,* the shaft [11] *11'* and the conic 16' of that [finger] *figure* has a tendency to rotate on the initial turning down of the nut [17] *17* irrespective of which profile 22H or 22N the nut *17* has. This impediment is amplified when the step bore nylon nut *nut* of FIG. 10 is used on the [screw 11] *11'* of FIG. 2 [or FIG. 10 while if]. *If* the stainless steel nut 17 of FIG. 11 is used, i.e., having a uniform threaded channel 21N, the problem is less pronounced.

*TWO PART DEVICE*

Referring to FIG. 12, the two part interdental device is generally shown as [10] *10.1*; and, consists of a shaft [11] *11.1* that includes a longitudinal smooth portion [12] *12.1* which tapers into a point or tip [14] *14.1* at [one end] *a distal end* and extends into a helical thread portion [15] *15.1* at [the other] *a proximate* end. The shaft [member] *11.1* has a length of approximately 3 inches [with the]. *The* helical thread portion *15.1 has a* length of about ⅜ of an inch [and]. *Shaft 11.1* is made of surgical stainless steel with a preferred diameter range of 0.025" (22 gauge) to 0.032" (20 gauge). A nut [17] *17.1* is formed of nylon such as Nylon Polyamide. Particularly suitable is a Nylon Polyamide pipe 6—6 available from Cadilac Plastics of Toronto, Ontario, Canada; this particular nylon will withstand temperatures of approximately 200° F., and remain rigid and hence, can be easy autoclaved. Its melting temperature is about 400° F. It also has a Rockwell hardness of R110–R120. The nut [17] *17.1,* has a channel [21] *21.1* therethrough, preferably as a smooth bore, as shown in FIG. 15. *The channel 21.1 preferably has a diameter sized to at least the root thread diameter of thread portion 15.1.* The nut [17] *17.1* then can be threaded onto the [threaded shaft 15] *thread portion 15.1, by cutting into the walls of channel 21.1,* part way down as shown in FIG. 12, and delivered to the surgeon this way.

Referring to FIG. 7, successive adjacent teeth $50_1$, $50_2$, $50_3$ and $50_4$, are shown referenced while the lower jaw is illustratively shown.

In order to immobilize one's jaw, while the patient is anesthetized, the device [10] *10.1* is pushed between the adjacent teeth $50_1$ and $50_2$ as shown in FIG. 12, and then, with a pair of pliers, the tip [14] *14.1* is bent into the phantom position and thereafter pushed between the next adjacent teeth $50_2$ and $50_3$ so as to extend in the fashion of FIG. 13. The tip [14] *14.1* is pulled taut, with a pair of pliers, in the direction of the arrow A so that the shaft 12 fits snug about the back of the tooth $50_2$ and with the truncated conical surface [20] *20.1* of the nut [17] *17.1* resting snug against adjacent teeth $50_1$ and $50_2$, as shown in phantom in FIG. 13. The tip [14] *14.1* is then moved with tweezers in the direction of arrow B and hence, into the phantom position; [and, then eventually]. *Tip 14.1 is* wrapped about [the] *a* segment of the helical [shaft 15] *thread 15.1,* disposed between nut [17] *17.1* and the adjacent teeth $50_1$ and $50_2$ in the fashion shown in FIG. 14. The distal end or tip [14] *14.1* of the shaft [12] *11.1* (the phantom portion referred to as [14' ] *14.1'* in FIG. 14) is cut away with a pair of wire cutters and discarded. Thereafter, the nut [15] *17.1* is turned down snug *by contacting and turning gripping surface 22.1H, which is hexagonal in shape, or 22.1N which is circular with a knurled outer surface,* on the helical thread *portion 15.1* to tighten the device [10] *10.1* and to anchor it about the tooth $50_2$, as shown in FIG. [3] *14.* Any excess [helical thread 14] *of shaft 11.1* that protrudes into the truncated conical recess [25] *25.1* of the nut [17] *17.1 may* be removed with wire cutters. Any exposed [ends] *proximate end* of the shaft [11 are] *11.1 is* therefore removed and no scratching or other abrasion takes place in the mouth of the wearer when implanted. *Wires or elastic loops W may then be inserted between installed devices 10.1 in a similar manner as shown in FIG. 9 with*

*wires or loops contacting and being held in position by truncated conical section 20.1.* There is virtually no blood letting.

We claim:

[1. A two part fixture adapted to act as an anchoring means in an interdental immobilization procedure comprising;

(a) a longitudinal deformable shaft defining a helical threaded portion that extends from one end and that transforms into a smooth cylindrical rod that terminates at a pointed distal end; and, (b) a screw member defining a bore therethrough adapted to matingly thread with the helical threaded portion, the length of the deformable longitudinal shaft being such as to permit the distal portion of the cylindrical rod to encircle a tooth and to loop about the shaft over a segment of the helical threaded portion.]

2. The fixture as claimed in claim [1] *49*, wherein the [screw member] *nut* is profiled as a conic.

3. The fixture as claimed in claim 2, wherein the conic is frusto-conical.

4. The [two part] fixture as claimed in claim 3 wherein the nut is nylon and the [elongated screw member] *shaft* is stainless steel.

5. The [two part] fixture as claimed in claim 3, wherein the [elongated screw member] *shaft* is stainless steel of a diameter in the range of 0.025" to 0.032" and the nut is nylon.

6. The [two part] fixture as claimed in claim 3, wherein the [elongated screw member] *shaft* is stainless steel of a diameter in the range of 0.025" to 0.032" and the nut is nylon, and the profile of the nut is a hexagon.

7. The fixture as claimed in claim 3, wherein the [elongated screw member] *shaft* is 3" long.

8. The [two part] fixture as claimed in claim [3] *50*, wherein the [elongated screw member] *shaft* is stainless steel and of a diameter in the range of 0.025" to 0.032" the nut is nylon and the [aperture] *channel* is [a] *of* smooth continuous [bore] *diameter*, sized to at least the root [threaded] *thread* diameter of the helical threaded portion.

9. The [two part] fixture as claimed in claim [3] *50*, wherein the [elongated screw member] *shaft* is stainless steel and of a diameter in the range of 0.025" to 0.032" and the nut is nylon and the [aperture] *channel* is *of* a two step [bore] *diameter*, a major *portion* sized to at least the diameter of the *shaft*, and a minor *portion* sized to at least the root thread diameter of the helical threaded portion.

10. The fixture as claimed in claim [3] *50*, wherein the helical [thread] *threaded portion* is a thread selected from the group of threads comprising a buttress form thread and a full depth V shaped thread.

11. The fixture as claimed in claim 3, wherein the shaft is surgical stainless steel and the [screw member] *nut* is a nylon polyamide.

12. The fixture as claimed in claim 3, wherein the shaft is surgical stainless steel and the [screw member] *nut* is a nylon polyamide wherein, the nylon polyamide has a Rockwell hardness of R110 to R120.

13. [A two part] *The* fixture as claimed in claim 2, wherein the nut is nylon and the [elongated screw member] *shaft* is stainless steel.

14. [A two part] *The* fixture as claimed in claim 2 wherein the [elongated screw member] *shaft* is stainless steel of a diameter in the range of 0.025" to 0.032" and the nut is nylon.

15. The [two part] fixture as claimed in claim 2, wherein the [elongated screw member] *shaft* is stainless steel of a diameter in the range of 0.025" to 0.032" and the nut is nylon, and the profile of the nut is a hexagon.

16. The fixture as claimed in claim 2, wherein the [elongated screw member] *shaft* is 3" long.

17. The [two part] fixture as claimed in claim [2] *50*, wherein the [elongated screw member] *shaft* is stainless steel and of a diameter in the range of 0.025" to 0.032" and the nut is nylon and the [aperture] *channel* is [a] *of* smooth continuous [bore] *diameter*, sized to at least the root thread diameter of the helical threaded portion.

18. The [two part] fixture as claimed in claim [2] *50*, wherein the [elongated screw member] *shaft* is stainless steel and of a diameter in the range of 0.025" to 0.032" nut is nylon and the *channel* is *of* two step [bore] *diameter*, have a major [bore] *portion* sized to at least the diameter of the [elongated screw member] *shaft*, and a minor [bore] *portion* sized to at least the root thread diameter of the helical threaded portion.

19. The fixture as claimed in claim [2] *50*, wherein the helical [thread] *threaded portion* is a thread selected from the group of threads comprising a buttress form thread and a full depth V shaped thread.

20. The fixture as claimed in claim 2, wherein the shaft is surgical stainless steel and the [screw member] *nut* is a nylon polyamide.

21. The fixture as claimed in claim 2, wherein the shaft is surgical stainless steel and the [screw member] *nut* is a nylon polyamide wherein, the nylon polyamide has a Rockwell hardness of R110 to R120.

22. The [two part] fixture as claimed in claim [1] *49*, wherein the nut is nylon and the [elongated screw member] *shaft* is stainless steel.

23. The [two part] fixture as claimed in claim [1] *49* wherein the [elongated screw member] *shaft* is stainless steel of a diameter in the range of 0.025" to 0.032" and the nut is nylon.

24. The [two part] fixture as claimed in claim [1] *49*, wherein the [elongated screw member] *shaft* is stainless steel of a diameter in the range of 0.025" to 0.032" and the nut is nylon, and the profile of the nut is a hexagon.

25. The fixture as claimed in claim [1] *49*, wherein the [elongated screw member] *shaft* is 3" long.

26. The [two part] fixture as claimed in claim [1] *50*, wherein the [elongated screw member] *shaft* is stainless steel and of a diameter in the range of 0.025" to 0.032" the nut is nylon and the [aperture] *channel* is [a] *of* smooth continuous [bore] *diameter*, sized to at least the root thread diameter of the helical threaded portion.

27. The [two part] fixture as claimed in claim [1] *50*, wherein the [elongated screw member] *shaft* is stainless steel and of a diameter in the range of 0.025" to 0.032" the nut is nylon and the [aperture] *channel* is [a] *of* two step [bore] *diameter*, a major [bore] *portion* sized to at least the diameter of the [elongated screw member] *shaft*, and a minor [bore] *portion* sized to at least the root thread diameter of the helical threaded portion.

28. The fixture as claimed in claim [1] *50*, wherein the helical [thread] *threaded portion* is a thread selected from the group of threads comprising a buttress form thread and a full depth V shaped thread.

29. The fixture as claimed in claim [1] *49*, wherein the shaft is surgical stainless steel and the [screw member] *nut* is a nylon polyamide.

30. The fixture as claimed in claim [1] *49*, wherein the shaft is surgical stainless steel and [the screw member] *the nut* is a nylon polyamide wherein, the nylon polyamide has a Rockwell hardness of R110 to R120.

31. A fixture for interdental immobilization comprising:

(a) an elongated [screw member carrying] *shaft comprising a detent* near [one] *a proximate* end [, a detent], and *a threaded portion* near the [other] opposite *distal* end [, a threaded portion];

(b) a first anchor means adapted to engage the detent; and, (c) a second anchor means defining a body portion and a [bore] *channel* and adapted to travel on the [screw member] *shaft*, the body portion having a cross-sectional area [traverse] *transverse* to the [bore] *channel* that in part, is smaller than at other axial locations along the body portion so as to accommodate and carry interconnecting elements [such as wires or elastics].

32. The fixture as claimed in claim 31 wherein [the interconnecting engagement member is a threaded shaft and] said first anchor member is a truncated conic defining a channel through which said shaft extends and wherein said second anchor means is integral with said [adjustably locating means (c)] *body portion* and includes means for engagement with said shaft [whereby the] to position said first and second anchor means relative to each other.

33. The fixture as claimed in claim 32 wherein said [means (c) for locating] *body portion* includes a bearing surface adapted to [locate said means (c) and said bearing anchor means relative to said first anchor means] *accommodate and carry said interconnecting elements.*

34. The fixture as claimed in claim 31 wherein the detent is in the form of an L.

35. The fixture as claimed in claim 34, wherein the [elongated screw member] *shaft* is "L" shaped having a distal arm with a threaded [shaft] *portion* and pointed tip thereon and a proximate arm.

36. The fixture as claimed in claim 34, wherein the [elongated screw member] *shaft* is "L" shaped having a distal arm with a threaded shaft and pointed tip thereon and a proximate arm [thus extends] *extending* through an obtuse angle into a [straight] *forwardly* inclined *straight* piece [that acts as a protrusion].

37. The fixture as claimed in claim 31 wherein the first anchor means has a slot for engagement with the detent.

38. The fixture as claimed in claim 37, wherein the [elongated screw member] is "L" shaped having a distal arm with a threaded [shaft] *portion* and pointed tip thereon and a proximate arm thus extends through an obtuse angle into a straight inclined piece that acts as a protrusion.

39. The fixture as claimed in claim 37 wherein the [bore] *channel* of the second anchor means is adapted to threadingly mate with and travel along the threaded portion.

40. The fixture as claimed in claim 39, wherein the [elongated screw member] *shaft* is "L" shaped having a distal arm with a threaded [shaft] *portion* and pointed tip thereon and a proximate arm [thus extends] *extending* through an obtuse angle into a [straight] *forwardly* inclined *straight* piece [that acts as a protrusion].

41. The fixture as claimed in claim 31 wherein the [bore] *channel* of the second anchor means is adapted to threadingly mate with and travel along the threaded portion.

42. The fixture as claimed in claim 41, wherein the [elongated screw member] *shaft* is "L" shaped having a distal arm with a threaded [shaft] *portion* and pointed tip thereon and a proximate arm [thus extends] *extending* through an obtuse angle into a [straight] *forwardly* inclined *straight* piece [that acts as a protrusion].

*43. A fixture adapted to act as an anchoring means in an interdental immobilization procedure comprising:*

*(a) a longitudinal deformable shaft having a proximate end and a distal end, the length of said shaft being sufficient to encircle a tooth and to permit said distal end to wrap about a segment of said shaft adjacent said proximate end;*

*(b) urging means engaging a portion of said shaft adjacent said proximate end for urging said proximate end away from said tooth to tighten said shaft about said tooth, said urging means urging said distal end against said tooth as said urging means urges said proximate end away from said tooth.*

*44. The fixture as claimed in claim 43, wherein said proximate end is securely fixed between said urging means and said tooth.*

*45. The fixture as claimed in claim 44, wherein said urging means is releasable to release said distal end from between said urging means and said tooth and to loosen said shaft about said tooth.*

*46. The fixture as claimed in claim 45, wherein said urging means comprises a concave distal end face forming a cavity and wherein said urging means comprises a channel through said urging means to receive said proximate end therein, said channel extending to said distal end face.*

*47. The fixture as claimed in claim 46, wherein said end face is contoured to permit entry of cutting means into said cavity for cutting said proximate end of said shaft protruding from said end of said channel.*

*48. The fixture as claimed in claim 47, wherein said distal end comprises a pointed tip.*

*49. The fixture as claimed in claim 43, wherein said urging means comprises a nut.*

*50. The fixture as claimed in claim 43, wherein said shaft comprises a helical threaded portion extending from one end, said helical threaded portion comprising a root thread diameter, and wherein said urging means comprises a nut with a channel through the nut to receive said proximate end of said shaft therethrough.*

*51. A method of securing an anchoring means in an interdental immobilization procedure comprising the steps of:*

*(a) pushing a longitudinal deformable shaft between adjacent teeth above the gum line so that the distal end of said shaft is on the lingual side of the teeth and the proximate end of said shaft remains on the buccal side the teeth;*

*(b) wrapping said distal end about the lingual side of one of the said adjacent teeth and pushing said distal end between said one tooth and the other adjacent tooth;*

*(c) wrapping said distal end about a segment of said shaft adjacent said proximate end;*

*(d) attaching urging means to said proximate end, said urging means for urging said proximate end away from said tooth;*

*(e) activating said urging means to urge said proximate end away from said tooth and to urge said distal end against said tooth and said urging means until said shaft tightly encircles said tooth.*

* * * * *